United States Patent [19]

Lam et al.

[11] 4,017,634
[45] Apr. 12, 1977

[54] INSECT GROWTH REGULATORS
[75] Inventors: Hsiao-Ling Lam, El Cerrito; Ferenc M. Pallos, Walnut Creek, both of Calif.
[73] Assignee: Stauffer Chemical Company, Westport, Conn.
[22] Filed: Jan. 12, 1976
[21] Appl. No.: 648,061
[52] U.S. Cl. .......................... 424/300; 260/455 A
[51] Int. Cl.² ............... A01N 9/20; C07C 155/02; C07C 155/03
[58] Field of Search ............... 260/455 A; 424/300
[56] References Cited
UNITED STATES PATENTS
3,816,502  6/1974  Pallos .......................... 260/455 A Primary Examiner—Lewis Gotts
Assistant Examiner—D. R. Phillips
Attorney, Agent, or Firm—Joel G. Ackerman

[57] ABSTRACT

Compounds having the formula.

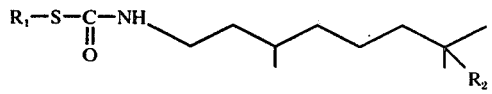

in which $R_1$ is lower alkyl, cycloalkyl, or cycloalkylalkyl, and $R_2$ is hydrogen or lower alkoxy. These compounds are selectively useful in controlling insects.

37 Claims, No Drawings

INSECT GROWTH REGULATORS

DESCRIPTION OF THE INVENTION

This invention relates to certain novel chemical compounds effective in combatting certain noxious insects. More particularly, this invention relates to thiocarbamates having the formula

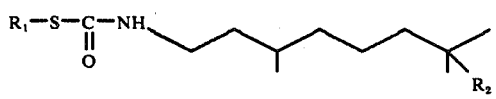

in which $R_1$ is lower alkyl, cycloalkyl or cycloalkylalkyl, and $R_2$ is hydrogen or lower alkoxy. The group occupying the $R_1$ position has preferably 3 to 5 carbon atoms, and may be for instance, methyl, ethyl, n-propyl, isopropyl, n-butyl, isobutyl, sec.-butyl, n-amyl, isoamyl, n-hexyl, and the like, cyclopropyl, cyclobutyl, cyclopentyl, and the like, or a cycloalkyl-alkyl radical such as cyclopropylmethyl, cyclobutylmethyl, cyclopropylethyl, and the like. These compounds have been found to have a utility in combatting certain insects in that they exert a disruptive influence upon the normal development of these insects. That is, they impede the metamorphosis of larvae to pupae and/or pupae to adults, resulting in the formation of abnormal insects which have not attained their full adult growth and which may also be nonviable or sterile. Such a treatment ultimately leads, at least indirectly, to destruction or partial elimination of a pest population.

In one aspect, the present invention relates to compounds useful in controlling certain insects, particularly in impeding the metamorphosis of such insects. In another aspect, this invention relates to a process for selectively controlling insects using such compounds. As shown by the test results which follow, these compounds have been found to possess particular effectiveness against insects belonging to the genera Musca, Culex, and Tenebrio.

Table 1 contains a list of representative compounds which may be prepared in accordance with the general procedure described herein. The compound numbers are assigned to each compound and are used throughout the remainder of the specification.

Table I

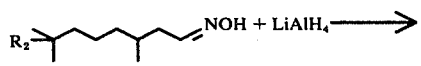

| Compound No. | $R_1$ | $R_2$ | $n_D^{30}$ |
|---|---|---|---|
| 1 | 2-methylbutyl | H | 1.4757 |
| 2 | 2-methylbutyl | —OCH₃ | 1.4794 |
| 3 | cyclopentyl | H | 1.4922 |
| 4 | cyclopentyl | —OCH₃ | 1.4945 |
| 5 | n-butyl | H | 1.4753 |
| 6 | n-butyl | —OCH₃ | 1.4797 |
| 7 | isobutyl | H | 1.4744 |
| 8 | isobutyl | —OCH₃ | 1.4789 |
| 9 | n-propyl | H | 1.4764 |
| 10 | n-propyl | —OCH₃ | 1.4810 |
| 11 | ▷—CH₂ | —OCH₃ | 1.4917 |

The compounds of the present invention may be prepared by a three-step process. In the first step, an aldehyde having the formula

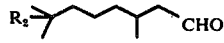

is reacted with hydroxylamine hydrochloride in the presence of a suitable base to produce the corresponding oxime by the reaction:

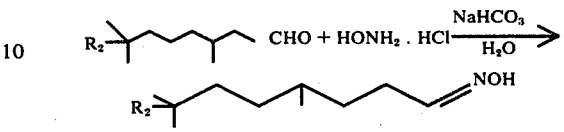

In the second step, the oxime is converted to the corresponding amine by a suitable reducing agent such as lithium aluminum hydride, according to the reaction:

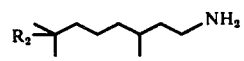

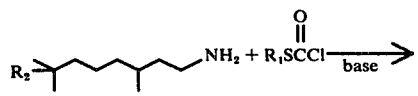

The amine is then reacted with an alkyl chlorothioformate to produce the final product:

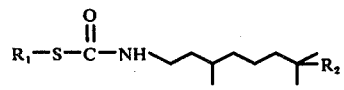

For example, N-dihydrocitronellyl-2-methylbutylthiocarbamate (compound 1 of Table 1 above) was prepared as follows:

a. In a 500 ml flask were placed 25 g (0.16 mole) 3,7-dimethyloctane-1-al (dihydrocitronellal) and 16 g (0.23 mole) hydroxylamine hydrochloride. There was then added, over a period of 30 minutes, a solution of 14 g (0.166 mole) sodium bicarbonate in 150 ml water. Evolution of a gas was observed. The mixture was stirred for two hours, during which time no temperature change was observed. The aqueous layer was saturated with sodium chloride, separated and extracted twice with benzene. The organic layers were combined, washed with water, dried over MgSO₄ and stripped. There was recovered 28.8 g (105% of theoretical yield) of 3,7-dimethyloctane-1-al oxime, $n_D^{30}$ 1.4491.

b. 20 g (0.117 mole) of the oxime obtained in step (a) in 150 ml of dry dioxane was slowly added to a flask containing 9 g (0.237 mole) lithium aluminum hydride in 150 ml ether. After addition was complete, the mixture was refluxed for 12 hours. Then, 40 ml water was slowly added to the mixture over a period of 1½ hours, with stirring and cooling with a salt-ice bath. The product was then extracted with three portions each of 200 ml ether, washed 3 times with water, dried over MgSO₄, and stripped. There was recovered 18 g of 3,7-dimethyloctyl amine (97% of theoretical yield), $n_D^{30}$ 1.4367.

c. To a solution of 1 g (0.025 mole) sodium hydroxide in 25 ml water, cooled with an ice bath, was added 3.15 g (0.02 mole) of the amine prepared in step (b), followed by 3.35 g (0.02 mole) of 2-methylbutyl chlorothioformate, dropwise with stirring. 10 ml of methylene chloride was used to rinse down the material on the walls of the flask. The reaction mixture was stirred in an ice bath for ½ hour, then in a bath at about 40° C for ½ hour, and finally at room temperature for ½ hour. The reaction mixture was then diluted with methylene chloride and water; the organic phase was washed twice with water and dried over $MgSO_4$. The dried solution was stripped. There was recovered 5.2 g (90% theoretical yield) of N-dihydrocitronellyl-2-methylbutyl thiocarbamate, $n_D^{30}$ 1.4757.

Insecticidal Evaluation Test

The degree of activity of a candidate compound to hinder or impede the metamorphosis of insects is measured by treating the penultimate larval stage of representative insects with the compound and examining them after their last molt toward the adult form for retention of immature features. Tests were conducted according to the following procedures:

a. Housefly larvea (*Musca domestica*, L.) - The test chemicals were diluted in acetone and topically applied in 1 µl. drops to pre-pupal housefly larvae about 4 days old, maintained at temperatures of about 27° C. A separate group of untreated larvae were similarly maintained as a control. The treated larvae and control were then placed in 55 × 17 mm glass Petri dishes with a filter paper disc covering the bottom. The larvae were then covered with a thin layer of slightly moist soil and stored at the same temperature until all control larvae had pupated and emerged as adults (about 5 days). Active compounds were determined as those which prevented the emergence of adults from the pupal cases. Tests are conducted at rates of from 10 µg/larva downwards. Table II lists the effective dose ($ED_{50}$) at which 50% of the flies failed to emerge.

b. Southern house mosquito (*Culex pipiens quinquefasciatus*, Say)—Tests were conducted on late 4th-instar larvae placed in a 6-ounce wax paper cup containing 100 mls of an aqueous solution of the test chemical. A separate group of untreated larvae was similarly maintained, as a control. The cups were covered with black tulle cloth and stored at 21° C for approximately 1 week during which time the larvae in the control group will pupate and emerge as adult mosquitos. Positive responses corresponded to larvae which either pupated and died before the adults emerged or in which the larvae metamorphosed to the adults but the adults died during the emerging process. The compounds were tested in concentrations ranging from 1 ppm downwards. Table II shows the effective concentration ($ED_{50}$) of the test compounds at which approximately 50% of the larvae were positively affected.

c. Yellow mealworm (Tenebrio molitor, L.) larvae were maintained at 28° C and 40% humidity. The test compounds were diluted in acetone and topically applied in 1 µl. drops to the abdomen of pupae which were less than 24 hours old. The treated pupae were incubated for 7 days at 28° C and 50% humidity until adults emerged (usually within 6 to 8 days). Emerged adults were graded as positive, negative or dead. Positive responses included abnormalities such as retention of urogomphi, gin traps, pupal cuticle, or the existence of adult-larval intermediates. Testing was done in decreasing rates starting from 10 µg/pupa. Table II below shows the dose of the test compound per pupa which resulted in positive responses or abnormalities in approximately 50% of the emerged adults, indicated as $ED_{50}$.

Table II

| | Approximate $ED_{50}$ Values | | |
|---|---|---|---|
| Compound No. | C. pipiens ppm | M. domestica µg/prepupa | T. molitor µg/pupa |
| 1 | 0.04 | >1.0 | 2.0 |
| 2 | 0.08 | >1.0 | 0.5 |
| 3 | 0.03 | 0.5 | 0.1 |
| 4 | 0.05 | >1.0 | 0.05 |
| 5 | 0.03 | >1.0 | 0.2 |
| 6 | 0.004 | >1.0 | 0.05 |
| 7 | 0.04 | 0.5 | 0.5 |
| 8 | 0.1 | >1.0 | 0.2 |
| 9 | 0.02 | 0.3 | 0.2 |
| 10 | 0.05 | >1.0 | 0.02 |
| 11 | 0.04 | >1.0 | 0.03 |

The compounds of this invention are generally embodied into a form suitable for convenient application. For example the compounds can be embodied into pesticidal compositions which are provided in the form of emulsions, suspensions, solutions, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; talc; pyrophyllite, diatomite; gypsum; clays, propellants, such as dichlorodifluoromethane, etc. If desired, however, the active compounds can be applied directly to feedstuffs, seeds, etc., upon which the pests feed. When applied in such a manner, it will be advantageous to use a compound which is not volatile. In connection with the activity of the presently disclosed pesticidal compounds, it would be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. The concentration of the active pesticide in the present compositions can vary within rather wide limits; they may contain from about 0.01 up to 80% by weight of the active pesticide compound.

The compounds of this invention can also be combined with baits in a conventional manner.

What is claimed is:

1. A compound having the formula

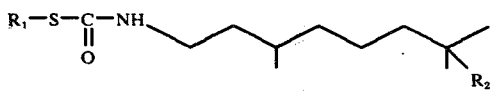

in which $R_1$ is lower alkyl, cycloalkyl, or cycloalkyl-alkyl and $R_2$ is hydrogen or lower alkoxy.

2. A compound according to claim 1 in which $R_1$ is lower alkyl.
3. A compound according to claim 2 in which $R_1$ is 2-methylbutyl.
4. A compound according to claim 2 in which $R_1$ is n-butyl.
5. A compound according to claim 2 in which $R_1$ is isobutyl.
6. A compound according to claim 2 in which $R_1$ is n-propyl.
7. A compound according to claim 1 in which $R_1$ is cycloalkyl.
8. A compound according to claim 7 in which $R_1$ is cyclopentyl.
9. A compound according to claim 1 in which $R_1$ is cycloalkyl-alkyl.
10. A compound according to claim 9 in which $R_1$ is cyclopropylmethyl.
11. A compound according to claim 1 in which $R_2$ is hydrogen.
12. A compound according to claim 1 in which $R_2$ is lower alkoxy.
13. A compound according to claim 1 in which $R_1$ is n-butyl and $R_2$ is methoxy.
14. A compound according to claim 1 in which $R_1$ is 2-methylbutyl and $R_2$ is hydrogen.
15. A compound according to claim 1 in which $R_1$ is 2-methylbutyl and $R_2$ is; methoxy.
16. A compound according to claim 1 in which $R_1$ is cyclopentyl and $R_2$ is hydrogen.
17. A compound according to claim 1 in which $R_1$ is cyclopentyl and $R_2$ is methoxy.
18. A compound according to claim 1 in which $R_1$ is n-butyl and $R_2$ is hydrogen.
19. A compound according to claim 1 in which $R_1$ is isobutyl and $R_2$ is hydrogen.
20. A compound according to claim 1 in which $R_1$ is isobutyl and $R_2$ is methoxy.
21. A compound according to claim 1 in which $R_1$ is n-propyl and $R_2$ is hydrogen.
22. A compound according to claim 1 in which $R_1$ is n-propyl and $R_2$ is methoxy.
23. A compound according to claim 1 in which $R_1$ is cyclopropylmethyl and $R_2$ is methoxy.
24. An insecticidal composition of matter comprising:
a. an insecticidal amount of a compound having a formula

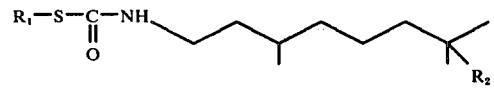

in which $R_1$ is lower alkyl, cycloalkyl, or cycloalkyl-alkyl and $R_2$ is hydrogen or lower alkoxy an inert carrier.
25. A method for selectively impeding the metamorphosis of insects comprising applying to the insect at its larval stage a metamorphosis-inhibiting effective amount of a compound having the formula

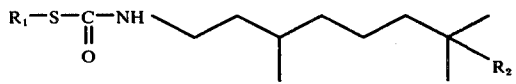

in which $R_1$ is lower alkyl, cycloalkyl, or cycloalkyl-alkyl and $R_2$ is hydrogen or lower alkoxy.

26. A method according to claim 25 in which $R_1$ is lower alkyl.
27. A method according to claim 26 in which $R_1$ is 2-methylbutyl.
28. A method according to claim 26 in which $R_1$ is n-butyl.
29. A method according to claim 26 in which $R_1$ is isobutyl.
30. A method according to claim 26 in which $R_1$ is n-propyl.
31. A method according to claim 25 in which $R_1$ is cycloalkyl.
32. A method according to claim 31 in which $R_1$ is cyclopentyl.
33. A method according to claim 25 in which $R_1$ is cycloalkyl-alkyl.
34. A method according to claim 33 in which $R_1$ is cyclopropylmethyl.
35. A method according to claim 25 in which $R_2$ is hydrogen.
36. A method according to claim 25 in which $R_2$ is lower alkoxy.1
37. A method according to claim 25 in which $R_1$ is n-butyl and $R_2$ is methoxy.

* * * * *